United States Patent [19]

Atchison et al.

[11] 4,269,727

[45] May 26, 1981

[54] RADIATION CURABLE FLAME RETARDANT COMPOSITIONS CONTAINING 2,2-DIALKYLPROPANE-1,3-DIOLBIS[BIS-(ACRYLOYLOXYLKYL) PHOSPHATES]

[75] Inventors: George J. Atchison; Gerald K. McEwen; Violete L. Stevens, all of Midland, Mich.

[73] Assignee: The Dow Chemical Company, Midland, Mich.

[21] Appl. No.: 82,191

[22] Filed: Oct. 5, 1979

Related U.S. Application Data

[62] Division of Ser. No. 960,383, Nov. 13, 1978.

[51] Int. Cl.³ .............................. C08F 2/48; C09F 9/09
[52] U.S. Cl. ........................ 252/188.3 R; 204/159.23; 204/181 E; 260/928
[58] Field of Search ................. 252/188.3 R; 260/928; 204/159.23, 181 E

[56] References Cited

U.S. PATENT DOCUMENTS 3,754,972  8/1973  de Majistrate .................. 260/928

*Primary Examiner*—Leland A. Sebastian
*Assistant Examiner*—Irwin Gluck

[57] ABSTRACT

Effective radiation curable flame retardant compositions include compounds of the formula:

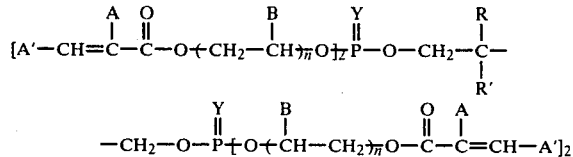

wherein A is hydrogen or methyl; A' is hydrogen, methyl, phenyl or halogen; n is 1 or 1.5 and when n is 1, B is hydrogen or methyl and when n is 1.5, B is hydrogen; Y is oxygen or sulfur; R and R' are hydrogen, methyl, chloromethyl or bromomethyl.

5 Claims, No Drawings

RADIATION CURABLE FLAME RETARDANT COMPOSITIONS CONTAINING 2,2-DIALKYLPROPANE-1,3-DIOLBIS[BIS-(ACRYLOYLOXYLKYL) PHOSPHATES]

CROSS-REFERENCE TO COPENDING APPLICATION

This application is a division of our copending application, U.S. Ser. No. 960,383, filed Nov. 13, 1978.

BACKGROUND OF THE INVENTION

The flammability of various products, especially those manufactured from plastic materials, has become a prime concern to fabricators and consumers. One of the more common approaches to solution of the problem is to incorporate, either by chemical reaction or physical blending, a flame-retardant compound into the product. Such compounds are usually compounds containing chlorine, bromine, phosphorous or nitrogen. It has long been recognized that some flame-retardant compounds are more effective in plastic formulations than other compounds. This is because the effectiveness of a compound is dependent not only on its flame-retardant capability but also on the ability of the compound to improve or modify, or at least not to detract from, other physical and chemical properties of the product.

SUMMARY OF THE INVENTION

This invention provides novel radiation curable flame-retardant compositions of normally flammable materials containing certain unsaturated phosphate compounds.

DETAILED DESCRIPTION OF THE INVENTION

The compositions with which the benefits of the invention are realized are those containing a photoinitiator and compounds of the formula:

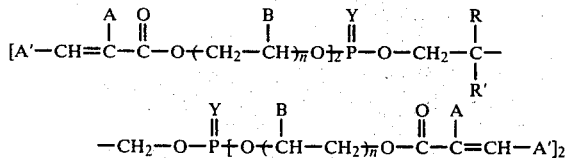

wherein A is hydrogen or methyl; A' is hydrogen, methyl, phenyl or halogen; n is 1 or 1.5 and when n is 1, B is hydrogen or methyl and when n is 1.5, B is hydrogen; Y is oxygen or sulfur; R and R' are independently hydrogen, methyl, chloromethyl or bromomethyl.

The compounds are easily prepared by the reaction of phosphorous oxyhalide with a hydroxyalkyl acrylate or methacrylate with the so-formed intermediate reacted with neopentyl glycol.

As an illustration of that preparation, 2,2-dibromomethylpropane-1,3-diolbis[bis(acryloyloxyethyl)phosphate] was prepared by the following procedure.

To a one-liter round bottom flask equipped with a mechanical stirrer and addition funnel was added 76.75 g $POCl_3$ (0.5 mole) in 500 ml of benzene. The addition funnel was charged with a solution of 116 g of 2-hydroxyethyl acrylate (1 mole), 101 g of triethylamine (1 mole) and 100 ml of benzene. The flask was cooled in an ice bath and the contents of the addition funnel was added dropwise such that the pot temperature remained below 20° C. After the addition was complete, the addition funnel was charged with a solution of 65.5 g of 2,2-bis(bromomethyl)-1,3-propanediol (0.25 mole), 50.5 g of triethylamine (0.5 mole) and 100 ml of benzene. This solution was added dropwise to the ice-cooled reaction pot. After the addition was complete, stirring was continued at ambient temperature for 12 hours. The precipitated $Et_3NHCl$ was removed by filtration and the solvent was stripped. The product was dissolved in $CH_2Cl_2$, washed with water and dried over anhydrous $MgSO_4$. The solvent was stripped from the product yielding 181 g (89 percent) of a slightly yellow liquid. Inhibition with the methyl ether of hydroquinone or phenothiazine or other known inhibitor is advised before completing the solvent removal.

Other compounds within the scope of the formula are made by the same procedure using the appropriate reactants to achieve the structure desired in the tetraester product. Also, other solvents and catalysts will be known to those skilled in the art.

The product is isolated and purified by known procedures.

The compounds are homopolymerizable and copolymerizable with a wide variety of olefinically unsaturated monomers and unsaturated resin precursors. Useful unsaturated monomers include both mono- and polyunsaturated compounds. Monounsaturated monomers include vinyl carboxylic acids, such as acrylic and methacrylic acids; vinyl nitrile monomers, such as acrylonitrile and methacrylonitrile; alkyl and hydroxyalkyl esters of vinyl carboxylic acids, such as methyl acrylate, butyl acrylate, cyclohexyl methacrylate, hydroxyethyl methacrylate, hydroxypropyl acrylate and the like where the alkyl group contains from 1 to about 8 carbon atoms; vinyl amide monomers such as acrylamide; and mixtures thereof.

Polyunsaturated monomers include ethylene glycol dimethacrylate; trimethylol propane trimethacrylate, methylene bisacrylamide and other similar monomers.

Resin systems for which the present flame-retardant agents are especially useful include an unsaturated polyester resin or a terminally unsaturated vinyl ester resin in admixture with at least one copolymerizable monomer. Generally, the resins are mixed with styrene for thermally cured reinforced articles but for radiation cure other monomers are more preferable such as the hydroxyalkyl acrylates. Mixtures of polyesters and vinyl esters are also contemplated. Generally, the resin comprises from 25 to 70 weight percent of the mixture and the monomer about 30 to 75 weight percent.

Unsaturated polyesters are prepared by a condensation reaction between a polyhydric alcohol and a dicarboxylic acid or anhydride thereof. Said alcohols include ethylene glycol, diethylene glycol, propylene glycol, dipropylene glycol and the like as well as polyalkylene glycols of higher molecular weight. Said acid includes unsaturated acids such as maleic acid, fumaric acid, itaconic acid or the like. Saturated dicarboxylic acids such as phthalic acid, isophthalic acid, tetrabromophthalic acid, chlorendic acid, adipic acid and the like may be used as partial replacement for the unsaturated acids to vary the degree of unsaturation of the polyester resin. The corresponding anhydrides are preferably employed when available.

The glycol or polyhydric alcohol component of the polyester is usually stoichiometric or in slight excess with respect to the sum of the acids. The excess of polyhydric alcohol seldom will exceed 20–25 percent and usually is about 2 to 10 percent.

These unsaturated polyesters may be generally prepared by heating a mixture of the polyhydric alcohol with the dicarboxylic acid or anhydride in the proper molar proportions at elevated temperatures, usually at about 150° C. to 225° C. for a period of time ranging from about 5 to 15 hours. Polymerization inhibitors such as t-butyl catechol may be advantageously added. It is also possible to prepare unsaturated polyesters directly from the appropriate oxide by copolymerization with an anhydride, e.g., propylene oxide can be used in place of propylene glycol and copolymerized with maleic anhydride or a mixture of maleic anhydride and phthalic anhydride. Further description of these well-known resins is unnecessary herein.

Terminally unsaturated vinyl ester resins are prepared by reacting about equivalent proportions of a polyepoxide resin and an unsaturated monocarboxylic acid wherein

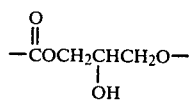

characteristic linkages are formed and the resulting resin has terminal, polymerizable unsaturated groups. For example, two equivalents of methacrylic acid may be reacted with two equivalents of a polyepoxide resin to produce a vinyl ester resin.

Vinyl ester resins are described in U.S. Pat. No. 3,367,992 to Bearden wherein dicarboxylic acid half esters of hydroxyalkyl acrylates or methacrylates are reacted with polyepoxide resins. Bowen in U.S. Pat. Nos. 3,066,112 and 3,179,623 describes the preparation of vinyl ester resins from monocarboxylic acids such as acrylic and methacrylic acid. Bowen also describes an alternate method of preparation wherein a glycidyl methacrylate or acrylate is reacted with the sodium salt of a dihydric phenol such as bisphenol A. Vinyl ester resins based on epoxy novolac resins are described in U.S. Pat. No. 3,301,743 to Fekete et al. Fekete et al. also describe in U.S. Pat. No. 3,256,226 vinyl ester resins wherein the molecular weight of the polyepoxide is increased by reacting a dicarboxylic acid with the polyepoxide resin as well as acrylic acid, etc. Other difunctional compounds containing a group which is reactive with an epoxide group, such as amine, mercaptan, and the like, may be utilized in place of the dicarboxylic acid. All of the above-described resins which contain the aforementioned characteristic linkages and terminal, polymerizable unsaturated groups, are classified herein as vinyl ester resins. The preparation of vinyl ester resins is fully disclosed in the above patents.

Additionally, it is meant to include within the definition of vinyl ester resins, those resins wherein the secondary hydroxyl group formed by the interaction of an epoxide group with a carboxylic acid group has been reacted with a dicarboxylic acid anhydride to produce pendant carboxylic acid groups. A variety of saturated and unsaturated anhydrides similar to those described as useful in preparing polyester resins may be used in proportions of at least about 0.1 mole of anhydride per equivalent of hydroxyl group up to an amount sufficient to react with each hydroxyl. A reaction temperature from about 25° C. to 150° C. is suitable and any of the well-known vinyl polymerization inhibitors may be added to prevent polymerization during the reaction.

Briefly, any of the known polyepoxides may be employed in the preparation of the vinyl ester resins of this invention. Useful polyepoxides are glycidyl polyethers of both polyhydric alcohols and polyhydric phenols, flame-retardant epoxy resins based on tetrabromo bisphenol A, epoxy novolacs, epoxidized fatty acids or drying oil acids, epoxidized diolefins, epoxidized diunsaturated acid esters as well as epoxidized unsaturated polyesters, so long as they contain more than one oxirane group per molecule. The polyepoxides may be monomeric or polymeric.

Preferred polyepoxides are glycidyl polyethers of polyhydric alcohols or polyhydric phenols having weights per epoxide group of about 150 to 2,000. These polyepoxides are usually made by reacting at least about 2 moles of an epihalohydrin or glycerol dihalohydrin with 1 mole of the polyhydric alcohol or polyhydric phenol, and a sufficient amount of a caustic alkali to combine with the halogen of the halohydrin. The products are characterized by the presence of more than one epoxide group per molecule, i.e., a 1,2-epoxy equivalency greater than one.

Unsaturated monocarboxylic acids include acrylic acid, methacrylic acid, halogenated acrylic or methacrylic acids, cinnamic acid and the like and mixtures thereof, and hydroxyalkyl acrylate or methacrylate half esters of dicarboxylic acids as described in U.S. Pat. No. 3,367,992 wherein the hydroxyalkyl group preferably has from two to six carbon atoms.

Useful dicarboxylic acid anhydrides to modify the vinyl ester resin include unsaturated anhydrides such as maleic anhydride, citraconic anhydric, itaconic anhydride, the various substituted maleic anhydrides and the like, as well as a variety of saturated anhydrides such as phthalic anhydride, chlorendic anhydride, tetrabromophthalic anhydride and the like.

A variety of copolymerizable monomers are available and suitable and include alkenyl aromatic monomers, alkyl esters of acrylic and methacrylic acid, vinyl acetate, acrylonitrile, diallyl maleate, diallyl phthalate, acrylic and methacrylic acid, and the like and mixtures thereof.

The esters of this invention are especially well adapted to cure by homopolymerization or copolymerization with photoinducement as by exposure to ultraviolet light. Methods and apparatus for such polymerizations are well known as shown, for example, in U.S. Pat. Nos. 3,661,576; 3,673,140 and 3,772,062 and many others.

The photopolymerizable flame retardants of this invention are bound in the fabricated product. Thus, the compound cannot be leached nor will it migrate out of the system as happens with nonpolymerizable additives.

The invention is illustrated in the following examples wherein all parts and percentages are by weight.

EXAMPLE 1

The compound 2,2-dibromomethylpropane-1,3-diol-bis[bis(acryloyloxyethyl)phosphate] having the structure:

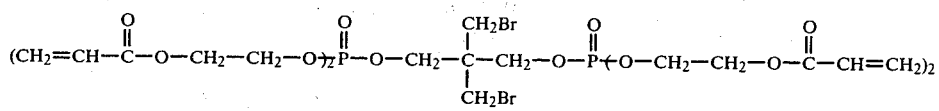

was prepared by the previously described procedure. The compound was coated on test panels and passed under the mercury arc source of a Linde Laboratory Photocure System at 100 feet per minute. After 15 passes, the compound was still liquid.

Other samples of the compound were mixed with 3 percent 2-phenyl-2-butoxyacetophenone (Trigonal-14), called hereafter Formulation A, coated on test panels and exposed to the mercury arc. The coating cured to a non-tacky film after one pass.

EXAMPLE 2

Formulations of the compound of Example 1 were made as follows:

Formulation B contained 77 percent of the compound, 20 percent n-butyl acrylate and 3 percent Trigonal-14.

Formulation C contained 49 percent of the compound, 29 percent of a vinyl ester resin, which was the diacrylate of the diglycidyl ether of bisphenol A, 19 percent of acetoxypropyl acrylate as a reactive diluent, and 3 percent Trigonal-14.

The formulations were coated on test panels and cured in an air atmosphere as in Example 1.

The cured films together with that of Formulation A were tested according to the following procedures.

FILM THICKNESS DETERMINATION

An Elcometer magnetic flux thickness gauge was used to read the thickness of cured films directly in mils. An uncoated test panel was used for setting the zero point of the gauge.

FILM ADHESION

A modification of the National Coil Coaters Association "Cross Hatch" tape test (3) was used. The slotted template (1½"×1½"×⅛" with six parallel slots 0.025"×1" spaced 0.1" apart) was held firmly on the test sample. One corner of the cutting edge of a fresh, single edge razor blade was used with sufficient pressure to cut through the coating to the substrate, successively making a cut in each slot. The template was then rotated 90° and six more cuts were made at right angles to and through the original cuts using the other corner of the razor blade cutting edge. Twenty-five squares 0.1"×0.1" were thus produced. The template was removed and Scotch® brand cellophane tape No. 600 was applied over the test area. The tape was rubbed with sufficient pressure to remove all air bubbles. After the test surface attained room temperature, the tape was removed by pulling sharply at a right angle to the test surface. A visual examination allowed an estimate of the percentage of coating remaining on the substrate in the test area.

HARDNESS

The hardness of a cured film was rated according to the hardness of a lead pencil that would just scratch it. Eagle Turquoise brand drawing pencils were used.

SOLVENT RESISTANCE (MEK RUBS)

Technical grade methyl ethyl ketone was applied to the surface of the cured film with a cotton swab. The MEK saturated swab was moved in a deliberate back-and-forth motion through a distance of approximately 1½" under a light pressure. The number of cycles necessary to adversely affect the film was measured.

EFFECT OF WATER

A drop of distilled water approximately 1" in diameter was placed on the cured coating and allowed to stand at room temperature. The coating was visually inspected during one hour at short intervals and the time required for blistering, peeling, etc., to take place was noted.

REVERSE IMPACT

The test was carried out using a Gardner Impact Tester. The coated and cured panel was positioned on the base plate of the testing anvil. The impact rod was dropped through the vertical guide tube calibrated in foot pounds of impact so as to force a round nose steel impact rod onto the reverse side of the test panel and thus deform the panel and coating. Scotch® brand cellophane tape No. 600 was then applied to the face of the impact dimple and removed as in the adhesion test. The impact in foot pounds which could be tolerated without causing a crack and/or peeling of the coating during the tape removal was taken as the measure of reverse impact value.

The results are shown in the following table.

TABLE

| Sample | Passes Under UV Source | Thickness in mils | % Adhesion | Pencil Hardness | MEK Double Rubs | Reverse Impact Inch Lbs | Effect of Water |
|---|---|---|---|---|---|---|---|
| A | 2 | 0.8 | 100 | 3H | >200 | <10 | Slight blush at one hour |
| A | 4 | 0.8 | 100 | 4H | >200 | <10 | No effect at one hour |
| B | 4 | 0.8 | 100 | 3H | >200 | <10 | No effect at one hour |
| B | 8 | 0.8 | 100 | 3H | >200 | <10 | No effect at one hour |
| C | 3 | 0.8 | 100 | 5H | >200 | <10 | No effect at one hour |
| C | 6 | 0.8 | 100 | 5H | >200 | <10 | No effect at one hour |

EXAMPLE 3

The compound 2,2-dimethylpropane-1,3-diolbis[bis-(acryloyloxyethyl)phosphate] was prepared by the previously described procedure.

The compound was coated on a test panel and exposed to the mercury arc as in the above examples. The coating cured to a soft, tacky film in 20 passes.

The compound was formulated with three percent Trigonal-14 and exposed to the UV source. After one pass, the cured solid had a slightly oily surface.

Coated on steel panels the formulation produced coatings having the following properties.

| Passes Under UV Source | Thickness in mils | % Adhesion | Pencil Hardness | MEK Double Rubs | Reverse Impact Inch lbs | Effect of Water |
|---|---|---|---|---|---|---|
| 1 | 0.6 | 0 | HB | >200 | <10 | Faint blistering at one hour |
| 3 | 0.6 | 12 | HB | >200 | <10 | Faint blistering at one hour |

We claim:

1. A radiation curable composition comprising (1) a compound of the formula:

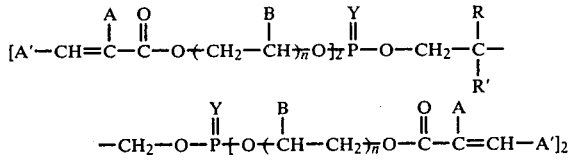

wherein A is hydrogen or methyl; A' is hydrogen, methyl, phenyl or halogen; n is 1 or 1.5 and when n is 1, B is hydrogen or methyl and when n is 1.5, B is hydrogen; Y is oxygen or sulfur; R and R' are hydrogen, methyl, chloromethyl or bromomethyl and (2) a photoinitiator.

2. The composition of claim 1 wherein said photoinitiator is 2-phenyl-2-butoxyacetophenone.

3. A radiation curable polymer composition comprising the polymerizate of at least one unsaturated monomer and a flame retarding amount of a compound of claim 1.

4. The radiation curable composition of claim 3 wherein said unsaturated monomer is an acrylic monomer.

5. A radiation curable composition comprising a flame retarding amount of the compound of claim 1 and an unsaturated polyester or a vinyl ester resin.

* * * * *